(12) United States Patent
Van Der Schaaf et al.

(10) Patent No.: US 6,417,363 B1
(45) Date of Patent: Jul. 9, 2002

(54) HETEROCYCLYL LIGAND CONTAINING RUTHENIUM AND OSMIUM CATALYSTS

(75) Inventors: Paul Adriaan Van Der Schaaf, Allschwil; Andreas Mühlebach, Frick; Andreas Hafner, Gelterkinden; Roman Kolly, Allschwil, all of (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/555,308

(22) PCT Filed: Nov. 24, 1998

(86) PCT No.: PCT/EP98/07574

§ 371 (c)(1),
(2), (4) Date: May 26, 2000

(87) PCT Pub. No.: WO99/29701

PCT Pub. Date: Jun. 17, 1999

(30) Foreign Application Priority Data

Dec. 4, 1997 (CH) .................................................. 2805/97

(51) Int. Cl.[7] .............................. B01J 31/24; C08F 4/44
(52) U.S. Cl. .......................... 546/6; 502/162; 502/156; 502/155; 526/161; 526/171; 526/172; 556/13; 556/136
(58) Field of Search .................. 526/172, 161, 526/171; 502/136, 155, 162; 556/13, 136

(56) References Cited

FOREIGN PATENT DOCUMENTS

| WO | 93/20111 | 10/1993 |
| WO | 96/04289 | 2/1996 |

OTHER PUBLICATIONS

Chaudret et al., Organometallics, vol. 15, No. 16, p. 3471–3473, date of issue: Aug. 6, 1996.*
Y. Guari et al., Organometallics, vol. 15, No. 16, (Aug. 1996), pp. 3471–3473.

* cited by examiner

Primary Examiner—David W. Wu
Assistant Examiner—R. Harlan
(74) Attorney, Agent, or Firm—Kevin T. Mansfield

(57) ABSTRACT

Penta- and hexa-coordinated, bridged ruthenium and osmium catalysts of the formula

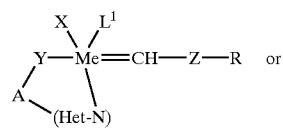 (Ia)

or

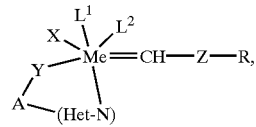 (Ib)

wherein Me is ruthenium or osmium; $L^1$ and $L^2$ are neutral ligands having electron donor properties;

X is an anionic ligand; Y is oxygen or sulphur; A is a direct bond, $C_1$–$C_4$alkylene or $C_2$–$C_4$alkylidene;

Z is a direct bond, oxygen, sulphur or the groups

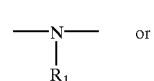 (B)

or

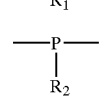 (C)

wherein $R_1$ and $R_2$ are hydrogen or hydrocarbon radicals; their preparation and their us in the synthesis of polymers, in the ring-closure metathesis of diolefins, in the cross metathesis of olefins and in the isomerisation of olefins are disclosed.

14 Claims, No Drawings

HETEROCYCLYL LIGAND CONTAINING RUTHENIUM AND OSMIUM CATALYSTS

The invention relates to novel penta- and hexa-coordinated, bridged ruthenium and osmium catalysts, to their preparation and to their use in the synthesis of polymers, in the ring-closure metathesis of diolefins, in the cross metathesis of olefins and in the isomerisation of olefins.

Thermal metathesis polymerisation of so-called strained cycloolefins, which has recently acquired great importance, requires suitable catalysts. Whereas, at first, systems consisting of catalyst and co-catalyst were used—see, for example, U.S. Pat. No. 4,060,468 and WO 93/13171—one-component catalysts have also been known for a relatively long time [Thoi, H. H., Ivin, K. J., Rooney, J. J., *J. Mot. Catal.* 15:245–270 (1982)]. So-called "metal carbenes", namely ruthenium and osmium complexes, having a =CR*R** group bonded to the metal central atom, are especially suitable for that application [WO 93/20111; Kanaoka, S., Grubbs, R. H., *Macromolecules* 28:4707–4713 (1995); Fraser, C., Hillmyer, M., Gutierrez, E., Grubbs, R. H., *Polym. Prepr.* 36:237–238 (1995); Schwab, P., France, M. B., Ziller, J. W., Grubbs, R. H., *Angew. Chem.* 107:2179–2181 (1995)]. That type of complex is also suitable for catalysing ring-closure in dienes (WO 96104289 or WO 97/06185).

The known metal carbene catalysts are penta-coordinated and contain as neutral e donor ligands, in addition to the group =CR*R**, identical tertiary phosphine groups bound to the central atom. The problem underlying the present invention is to prepare further, improved catalysts for the synthesis of polymers, for the ring-closure metathesis of olefins and for the isomerisation of olefins.

It has been found, surprisingly, that penta- and hexa-coordinated ruthenium and osmium complexes with a mono- or bi-cyclic, aromatic heterocyclyl group containing at least one nitrogen atom that is coordinated with the ruthenium or osmium central atom are excellent catalysts for metathesis reactions and the ring-closure of dienes. By suitable selection of the neutral ligands it is possible to control the reactivity, for example the latency, in a specific manner over a wide range.

The invention relates to compounds of formulae

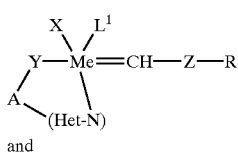

(Ia)

and

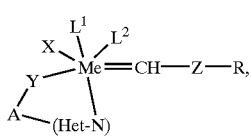

(Ib)

wherein Me is ruthenium or osmium;
L$^1$ and L$^2$ are neutral ligands having electron donor properties;
X is an anionic ligand;
Y is oxygen or sulfur;
A is a direct bond, C$_1$–C$_4$alkylene or C$_2$–C$_4$alkylidene;
Z is a direct bond, oxygen, sulfur or the groups

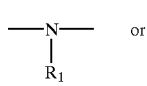

(B)

or

(C)

wherein R$_1$ and R$_2$ are hydrogen or hydrocarbon radicals;
R is a hydrocarbon radical; and
Het-N is mono- or bi-cyclic, aromatic heterocyclyl having at least one nitrogen atom that is coordinated with Me;
and to isomers thereof.

The invention relates also to compounds of formulae Ia and Ib including all cases of isomerism, for example of the coordination isomerism or bond isomerism type, especially stereoisomers, that arise as a result of different spatial arrangement of the ligands about the central atom. Compounds of formula Ia include the following isomeric structures of formulae

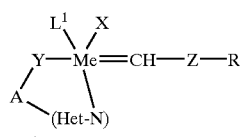

(I′a)

and

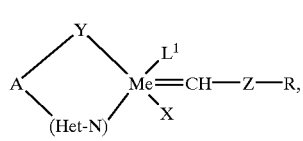

(I″a)

wherein L$^1$, X, Y, A, Z, R and Het-N are as defined hereinbefore.

The invention relates also to stereoisomeric compounds that arise as a result of the presence of a chiral centre in one of the mentioned ligands or in a side chain. Those cases of isomerism include optically pure enantiomers, diastereoisomers and also racemic mixtures.

The definitions and terms used in the context of the description of the present invention preferably have the following meanings:

The anionic ligand X is, for example, hydride (H$^-$) or is derived from inorganic or organic acids and, by way of example, is selected from the group of the halides, for example fluoride, chloride or bromide, fluoro complexes of the type BF$_4^-$, PF$_6^-$, SbF$_6^-$ or AsF$_6^-$, anions of oxy acids, for example carbonate, sulfate, phosphate, arsenate or antimonate, sulfonates, for example methanesulfonate, ethanesulfonate, n-propanesulfonate, n-butanesulfonate, trifluoromethanesulfonate (triflate), unsubstituted benzenesulfonate or p-toluenesulfonate, or benzenesulfonate or p-toluenesulfonate substituted by C$_1$–C$_4$alkyl, C$_1$–C$_4$alkoxy or by halogen, especially fluorine, chlorine or bromine, for example tosylate, mesylate, brosylate, p-methoxy- or p-ethoxy-benzenesulfonate or pentafluorobenzenesulfonate, phosphonates, for example methyl phosphonate, ethyl phosphonate, propyl phosphonate, butyl phosphonate, phenyl phosphonate, p-methylphenyl phosphonate or benzyl phosphonate, carboxylates derived, for example, from a $C_1$–$C_8$carboxylic acid, for example formate, acetate, propionate, butyrate, benzoate, phenyl acetate, mono-, di- or tri-chloroacetate or trifluoroacetate, alcoholates, acetylides and anions of cyclopentadiene.

Further suitable anions are $C_3$–$C_{18}$—, preferably $C_5$–$C_{14}$— and especially $C_5$–$C_{12}$—, acetylides corresponding to the formula $R_w$—C≡C⁻ wherein $R_w$ is $C_1$–$C_{16}$alkyl, preferably α-branched $C_3$–$C_{12}$alkyl, for example of the formula $R_xR_yR_zC$—, or is unsubstituted phenol or benzyl or phenol or benzyl mono- to tri-substituted by $C_1$–$C_4$alkyl or $C_1$–$C_4$alkoxy. Examples include isopropyl-, iso- and tert-butyl-, phenyl-, benzyl-, 2-methyl-, 2,6-dimethyl-, 2-isopropyl-, 2-isopropyl-6-methyl-, 2-tert-butyl-, 2,6-di-tert-butyl- and 2-methyl-6-tert-butylphenyl-acetylide.

Further suitable anionic ligands are also ligands that are derived from cyclopentadiene, for example cyclopentadienyl, and also indenyl, allyl, metallyl and crotyl.

Especially preferred anionic ligands are H⁻, F⁻, Cl⁻, Br⁻, $BF_4^-$, $PF_6^-$, $SbF_6^-$, $AsF_6^-$, $CF_3SO_3^-$, $C_6H_5$–$SO_3^-$, $4CH_3$–$C_6H_5$—$SO_3^-$, 3,5-dimethyl-$C_6H_5$—$SO_3^-$, 2,4,6-trimethyl-$C_6H_5$—$SO_3^-$ and 4-$CF_3$—$C_6H_5$—$SO_3^-$ and also cyclopentadienyl (Cp⁻).

In the compounds of formulae Ia and Ib, the neutral ligand $L^1$, and also the ligand $L^2$ denoting a neutral ligand, is tertiary phosphine having from 3 to about 40, preferably from 3 to 30, and especially from 3 to 18, carbon atoms. Preference is given to the tertiary phosphine of formula

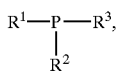
(II)

wherein $R^1$, $R^2$ and $R^3$ are, each independently of the others, $C_1$–$C_{20}$alkyl, $C_4$–$C_{12}$cycloalkyl, $C_2$–$C_{11}$heterocycloalkyl, $C_6$–$C_{16}$aryl, $C_2$–$C_{15}$heteroaryl or $C_7$–$C_{16}$aralkyl, wherein alkyl, cycloalkyl, heterocycloalkyl, aryl, heteroaryl or aralkyl are unsubstituted or substituted by one or more substituents selected from the group consisting of $C_{1-C_6}$alkyl, $C_1$–$C_6$alkoxy, $C_1$–$C_6$haloalkyl, $C_6$–$C_6$aryl, —$NO_2$, sulfo, ammonium and halogen; $R^1$ and $R^2$ together are tetra- or penta-methylene that is unsubstituted or substituted by $C_{1-C_6}$alkyl, $C_1$–$C_6$haloalkyl, —$NO_2$ or by $C_1$–$C_6$alkoxy, or tetra- or penta-methylene that is condensed with one or two 1,2-phenylene and that is unsubstituted or substituted by $C_1$–$C_6$alkyl, $C_1$–$C_6$haloalkyl, —$NO_2$ or by $C_1$–$C_6$alkoxy, and $R^3$is as defined above.

Examples of alkyl are methyl, ethyl, n- and iso-propyl and n-, sec- and tert-butyl, and also pentyl, hexyl, heptyl, octyl, nonyl, decyl, undecyl and dodecyl and isomers thereof. An example of alkyl substituted by aryl is benzyl. Examples of alkoxy are methoxy, ethoxy, n- and isopropoxy and also n-, sec- and tert-butoxy. Examples of cycloalkyl are cyclo-butyl, -heptyl and -octyl and, especially, -pentyl and -hexyl.

Examples of aryl are phenyl and naphthyl. Examples of aryloxy are phenoxy and naphthyloxy. Aralkyl is preferably benzyl.

Examples of substituted cycloalkyl, aryl and aralkyl are cyclopentyl and cyclohexyl substituted by mono-, di- or tri-methyl or -methoxy or by mono-, bis- or tris-(trifluoromethyl), and also phenyl and benzyl substituted by those substituents.

Heterocycloalkyl preferably contains from one to four heteroatoms, the heteroatoms being selected from the group oxygen, sulfur and nitrogen. Examples of heterocycloalkyl include tetrahydrofuryl, pyrrolidinyl, piperazinyl and tetrahydrothienyl. Examples of heteroaryl include furyl, thienyl, pyrrolyl, pyridyl and pyrimidinyl.

Preference is given to compounds of formulae Ia and Ib wherein one or two ligands from the group $L^1$ and $L^2$ correspond to a tertiary phosphine of formula II in which $R^1$, $R^2$ and $R^3$ are identical substituents, for example $C_1$–$C_4$alkyl or phenyl. Preference is furthermore given to phosphines of formula II having bulky, sterically demanding substituents, for example cyclic or branched, especially α,α-di-branched and more especially α-branched, alkyl groups.

Preference is given also to compounds of formulae Ia and Ib wherein one or two ligands from the group $L^1$ and $L^2$ correspond to a tertiary phosphine of a compound of formula II in which $R^1$, $R^2$ and $R^3$ are, each independently of the others, $C_1$–$C_8$alkyl, $C_5$- or $C_6$-cycloalkyl, $C_6$–$C_{10}$aryl or $C_7$–$C_{17}$aralkyl, wherein alkyl, cycloalkyl, aryl and aralkyl are unsubstituted or substituted by from one to three substituents selected from the group methyl, methoxy, ethyl, ethoxy, sulfo, trimethylamino, triethylamino and trifluoromethyl.

Special preference is given to phosphines of formula II wherein $R^1$, $R^2$ and $R^3$ are methyl, ethyl, n- or iso-propyl, n-, iso-, sec- or tert-butyl, 1-, 2- or 3-pentyl, 1-, 2-, 3- or 4-hexyl, cyclopentyl, cyclohexyl, phenyl, naphthyl or benzyl. More especially, (iso-$C_3H_7$)$_3$P, (sec-$C_4H_9$)$_3$P, ($C_5H_9$)$_3$P and ($C_6H_{11}$)$_3$P are preferred.

Het-N denoting monocyclic heterocyclyl contains, in total, from one to three nitrogen heteroatoms and five or six ring atoms. Het-N denoting bicyclic heterocyclyl contains, in total, from one to four nitrogen heteroatoms and from seven to twelve ring atoms.

Monocyclic heterocyclyl containing, in total, one or two nitrogen heteroatoms and bicyclic heterocyclyl containing from one to three nitrogen heteroatoms may also contain, as further heteroatoms, oxygen or sulfur.

Het-N may, in addition, be substituted by substituents from the group halogen, for example chlorine, bromine or iodine, hydroxy, oxo, etherified or esterified hydroxy, for example $C_1$–$C_4$alkoxy, for example methoxy or tert-butoxy, $C_1$–$C_4$alkoxycarbonyl, for example ethoxycarbonyl, sulfo, carboxy, aryl, for example phenyl, carbamoyl, amino, mono- or di-$C_1$–$C_4$alkylamino, for example dimethylamino, and $C_1$–$C_8$alkyl, for example methyl, ethyl, isopropyl, n-propyl, n-butyl, sec-butyl, tert-butyl or neopentyl. Acid groups may, depending on the pH conditions, be present in salt form, for example in the form of a sodium or potassium salt. Het-N may, in addition, be substituted by a butanediylidene group to form a fused bicyclic aromatic group which is coordinated with Me via the nitrogen atom.

Monocyclic heterocyclyl containing, in total, from one to three nitrogen heteroatoms and five or six ring atoms is preferably selected from the group consisting of pyrrole, imidazole, pyrazole, pyridine, pyrimidine, pyrazine, pyridazine and triazine. Bicyclic heterocyclyl containing, in total, from one to four nitrogen heteroatoms and from seven to twelve ring atoms is preferably selected from the group indole, quinoline, isoquinoline, purine and pteridine. Monocyclic heterocyclyl including the heteroatoms oxygen or sulfur is, for example, oxazole, thiazole or thiadiazole.

In compounds of formulae Ia and Ib, Z is a direct bond, oxygen, sulfur or the groups

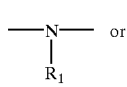
(B)

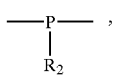

wherein $R_1$ and $R_2$ are hydrogen or a hydrocarbon radical. The term hydrocarbon radical for $R_1$ and $R_2$ includes the definitions mentioned hereinbefore under compounds (II) for $R^1$, $R^2$ and $R^3$, especially the mentioned aliphatic, cycloaliphatic or cycloaliphatic-aliphatic radicals, carbocyclic aryl radicals or aryl-aliphatic radicals having the mentioned further substituents and also the heterocyclic groups defined for Het-N having the mentioned further substituents.

In compounds of formulae Ia and Ib wherein Z denotes the groups B or C, $R_1$ and $R_2$ are preferably hydrogen, $C_1$–$C_{20}$alkyl, $C_3$–$C_8$cycloalkyl, $C_3$–$C_7$heterocycloalkyl, $C_6$–$C_{14}$aryl or $C_4$–$C_{15}$heteroaryl, wherein alkyl, cycloalkyl, heterocycloalkyl, aryl and heteroaryl are unsubstituted or substituted by one or more substituents from the group $C_1$–$C_4$alkyl, $C_1$–$C_4$haloalkyl, $C_1$–$C_4$alkoxy, $C_6$–$C_{10}$aryl, $C_6$–$C_{10}$aryloxy, hydroxy, oxo, carboxy, sulfo, —NO$_2$ and halogen.

In compounds of formulae Ia and Ib, R is a hydrocarbon radical having the definitions specified for $R_1$ and $R_2$.

When Z in compounds of formulae Ia and Ib is sulfur, R is preferably aryl, for example phenyl that is unsubstituted or substituted by one or more substituents from the group consisting of $C_1$–$C_6$alkyl, $C_1$–$C_6$alkoxy, $C_1$–$C_6$haloalkyl, hydroxy, carboxy, nitro, sulfo, ammonium and halogen.

Furthermore, when Z in compounds of fomulae Ia and Ib denotes groups B and C, the substituents $R_1$ and $R_2$ may be connected to one another, with the inclusion of phosphorus or, preferably, nitrogen, to form a heterocycle which may be unsaturated or partially or completely saturated and provided with further substituents, for example alkyl, alkoxy, halogen, hydroxy or oxo.

In compounds Ia and Ib, Y is preferably oxygen. A is preferably a direct bond when Het-N is bicyclic heterocyclyl, or, when Het-N is monocyclic heterocyclyl, A is $C_1$–$C_4$alkylene or $C_2$–$C_4$alkylidene. In such preferred embodiments, Z is a direct bond or is sulfur.

A denoting $C_1$–$C_4$alkylene is, for example, methylene, 1,2-ethylene, 1,3-propylene or 1,2-propylene, which may be substituted by, for example, halogen, for example chlorine, one or two hydroxy, or by aryl, for example phenyl. Phenyl may in turn be substituted by halogen, for example chlorine, hydroxy, amino, mono- or di-$C_1$–$C_4$alkylamino, for example dimethylamino, or by protected hydroxy, for example tert-butoxy or tert-butyidimethylsilyloxy.

A denoting $C_2$–$C_4$alkylidene is, for example, ethylidene or isopropylidene, each of which in addition may be substituted by aryl, for example phenyl.

A is preferably methylene, methylene substituted by ethylenedioxy or one or two hydroxy or phenyl, it being possible for phenyl to be substituted by halogen, for example chlorine, dimethylamino, or by tert-butyldimethylsilyloxy, ethylidene, or ethylidene or isopropylidene 1- or 2-substituted by phenyl.

The invention relates preferably to a selected group of compounds of formula Ia wherein $L^1$ is (iso-$C_3H_7$)$_3$P, (sec-$C_4H_9$)$_3$P, ($C_5H_9$)$_3$P or ($C_6H_{11}$)$_3$P; X is chlorine, Y is oxygen; A is methylene, methylene substituted by ethylenedioxy, one or two hydroxy, one or two phenyl or by one or two substituted phenyl from the group 4-chlorophenyl, 4-dimethylaminophenyl and 4-tert-butyidimethylsilylphenyl, ethylidene, or ethylidene or iso-propylidene 1- or 2-substituted by phenyl; Z is a direct bond or is sulfur; R is $C_1$–$C_4$alkyl, phenyl or phenyl substituted by $C_1$–$C_4$alkyl; and N-Het is pyridyl that is coordinated in the 1-position with Me and connected in the 2-position to A, and to isomers of those compounds.

The invention relates especially to a selected group of compounds of formula

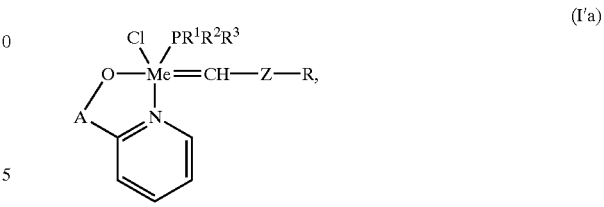

wherein $R,^1$, $R^2$ and $R^3$ are isopropyl, sec-butyl, cyclopentyl or cyclohexyl; A is methylene, methylene substituted by ethylenedioxy, one or two hydroxy, one or two phenyl or by one or two substituted phenyl from the group 4-chlorophenyl, 4-dimethylaminophenyl and 4-tert-butyldimethylsilylphenyl, ethylidene, or ethylidene or iso-propylidene 1- or 2-substituted by phenyl; Z is a direct bond or is sulfur and R is $C_1$–$C_4$alkyl, phenyl or phenyl substituted by $C_1$–$C_4$alkyl, and to isomers of those compounds.

The invention relates more especially to a selected group of compounds of formula I'a wherein $R^1$, $R^2$ and $R^3$ are isopropyl or cyclohexyl; A is methylene, methylene substituted by ethylenedioxy, one or two hydroxy, one or two phenyl or by one or two substituted phenyl from the group 4-chlorophenyl, 4-dimethylaminophenyl and 4-tert-butyidimethylsilylphenyl, ethylidene, or ethylidene or iso-propylidene 1- or 2-substituted by phenyl; Z is a direct bond and R is phenyl, and to isomers of those compounds.

The invention relates also more especially to the compounds mentioned in the Examples.

The invention relates also to a process for the preparation of compounds of formulae Ia and Ib, which process comprises reacting a compound of formula

or

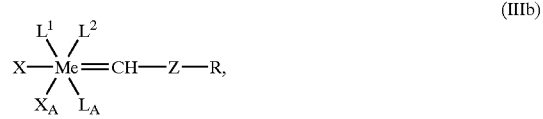

wherein $X_A$ and $L_A$ are leaving groups of the substrate and $L^1$, $L^2$, X, Z and R are as defined for formulae Ia and Ib, with a hydroxy or mercapto compound of formula

wherein Y, A and Het are as defined for formulae Ia and Ib, or with a reactive functional derivative thereof, with $X_A$ and $L_A$ being removed, and, if desired, isolating an obtainable compound of formula Ia or Ib and/or reacting an obtainable compound of formula Ia or Ib to form a different compound of formula Ia or Ib.

In a compound of formula IIIa or IIIb, the leaving groups $X_A$ and $L_A$ preferably have the definitions of X, for example chlorine, or of L¹, for example (iso-C₃H₇)₃P, (sec-C₄H₉)₃P, (C₅H₉)₃P or (C₆H₁₁)₃P. Compounds of formula IIIa are known. Their preparation is described in, for example, WO 97/06185. Compounds of formula IIIb can be prepared in a manner known per se, for example by reacting a compound of formula IIIa with a tertiary phosphine corresponding to a compound of formula II.

In a compound of formula IV, Het-N is preferably 1-pyridyl, A is methylene, methylene substituted by ethylenedioxy or by one or two hydroxy or phenyl, ethylidene, or ethylidene or isopropylidene 1- or 2-substituted by phenyl, and Y is preferably oxygen. A reactive functional derivative of a compound of formula IV is, for example, an alcoholate, which is prepared, for example, by reacting the hydroxy compound (IV) with n-butyllithium. Compounds of formula IV are known. Pyridylcarbinols IV and their preparation are known; see, for example, J. P. Wibout et al in *Recl. Trav. Chim.* Pays-Bas 70 (1951), 1054.

The process according to the invention is advantageously performed by dissolving the compound of formula IV in a solvent and then adding the compounds IIIa or IIIb. In a preferred variant of the process, the compound IV is converted into a reactive derivative, for example into the alcoholate, by reaction with n-butyllithium. The mass ratio of compounds of formulae IIIa and IIIb to compounds of formula IV is usually in the range from 1:1 to 1:10, a ratio in the range from 1:1 to 1:5 being preferred. The reaction advantageously takes place in a non-polar, aprotic solvent, for example in diethyl ether, at a temperature in the range from −80° C. to room temperature.

Compounds of formulae Ia and Ib wherein Z is oxygen, sulfur or the groups B or C may be prepared by subsequent reaction of a compound (Ia) or (Ib) wherein Z is a direct bond, for example by reaction of a corresponding phenylcarbene compound with a vinyl ether, vinyl thioether, vinylamine or vinylphosphine of the formula

$$R_b=CH-Z-R \quad (V),$$

wherein $R_b$ is a removable leaving group of the reagent, for example the CH₂ group, and Z is as defined for formulae Ia and Ib. The subsequent reaction is performed by introducing the compound (Ia) or (Ib), for example a phenylcarbene compound, into a solvent and adding the relevant vinyl ether, vinyl thioether, vinylamine or vinylphosphine.

The invention relates also to a composition comprising (a) dicyclopentadiene or a further strained cycloolefin or dicyclopentadiene in admixture with a further strained cycloolefin and (b) a catalytic amount of at least one compound of formula Ia or Ib, wherein L¹, X, Y, A, Z, R and Het-N have the definitions mentioned, or an isomer thereof, and, optionally, further additives for polymers.

Dicyclopentadiene is the dimer of cyctopentadiene, is known and commercially available and has the formula

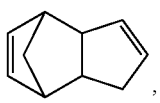

Dicyclopentadiene is known to form, together with further cyclopentadiene, so-called Diels-Alder adducts and thus forms oligomers that are also suitable for use. According to the invention, there may be present in the composition pure dicyclopentadiene, oligomers of dicyclopentadiene or mixtures thereof. The oligomers correspond to the formula

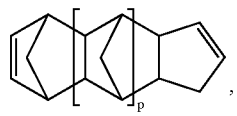

wherein p is a number from 1 to 100, preferably from 1 to 50, especially from 1 to 20, and more especially from 1 to 10.

So-called strained cycloolefins, which may be present as comonomers in the composition according to the invention, are known.

The cyclic olefins may be monocyclic or polycyclic, fused and/or bridged ring systems, for example having from two to four rings, which are unsubstituted or substituted and may contain heteroatoms, for example O, S, N or Si, in one or more rings and/or fused aromatic or heteroaromatic rings, for example o-phenylene, o-naphthylene, o-pyridinylene or o-pyrimidinylene. The individual cyclic rings may contain from 3 to 16, preferably from 3 to 12, and especially from 3 to 8, ring members. The cyclic olefins may contain further non-aromatic double bonds, depending on the ring size, preference being given to from 2 to 4 such additional double bonds. The ring substituents are substituents that are inert, that is to say that do not impair the chemical stability of the ruthenium and osmium compounds. The cycloolefins are strained rings or ring systems.

When the cyclic olefins contain more than one double bond, for example from 2 to 4 double bonds, then, depending on the reaction conditions, the monomer selected and the amount of catalyst, cross-linked polymerisates may also be formed.

Fused-on alicyclic rings contain preferably from 3 to 8, especially from 4 to 7, and more especially 5 or 6, ring carbon atoms.

The cyclic olefins present in the composition, which are capable of being polymerised with the aid of the catalysts according to the invention, are known and are described, for example, in WO 96/20235.

The comonomeric cycloolefins may be present in an amount of from 0.01 to 99% by weight, preferably from 0.1 to 95% by weight, especially from 1 to 90% by weight, and more especially from 5 to 80% by weight, based on the monomers present in the composition. Most preferably norbornene is present as comonomer in amounts of, for example, from 20 to 60% by weight.

The dienes which are capable of being ring-closed with the aid of the catalysts according to the invention, are described, for example, by Miller et al. [Miller, S. J., Blackwell, H. E., Grubbs, R. H., *J. Am. Chem. Soc.* 118:9606–9614 (1996)] or by Grubbs et al. [Grubbs, R. H., Miller, S. J., Fu, G. C., *Acc. Chem. Res.* 28:446–452 (1995)].

The catalysts according to the invention may also be used for breaking down unsaturated polymers or for the isomerisation of double bonds, as has already been described for catalysts based on ruthenium by McGrath and Grubbs [McGrath, D. V., Grubbs, R. H., *Organometallics* 13:224 (1994)].

The composition according to the invention may comprise inert solvents. A special advantage is that, in the case of liquid monomers, metathesis polymerisation can be carried out without the use of a solvent. A further advantage is that the polymerisation can be carried out even in water, polar and protic solvents or water/solvent mixtures. In those cases, it is advantageous within the context of the present invention to use a surfactant.

Suitable inert solvents are, for example, protic-polar and aprotic solvents, which may be used on their own or in mixtures of at least two solvents. Examples are: ethers (dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons etc.

Compositions according to the invention comprising DCPD are not sensitive to oxygen and moisture, which makes it possible to store them and to carry out the reaction without protective gas.

In the context of the present invention, a catalytic amount means preferably an amount of from 0.001 to 20 mol %, especially from 0.01 to 15 mol % and more especially from 0.01 to 10 mol %, based on the amount of the monomer. On account of the high thermocatalytic activity, special preference is given to amounts of from 0.001 to 2 mol %.

The composition according to the invention used for the polymerisation can be prepared immediately prior to the polymerisation or can be used as a pre-formulated mixture, because the catalysts used have an especially high degree of stability. The mixture can even be stored as a ready-to-use formulation for a relatively long time before the polymerisation, which is advantageous for use on a large scale.

The composition according to the invention may comprise additives that are suitable for polymers, which additives are preferably used as formulation adjuvants for improving the chemical and physical properties. The adjuvants may be present in surprisingly high amounts without having an adverse effect on the polymerisation, for example in amounts of up to 70% by weight, preferably from 1 to 70% by weight, especially from 5 to 60% by weight, more especially from 10 to 50% by weight and very especially from 10 to 40% by weight, based on the composition. A great number of such adjuvants are known and are given by way of example in the following list of adjuvants:

1. Anti-oxidants 1.1. Alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols that are linear or branched in the side chain, for example 2,6-dinonyl-4-methylphenol, 2,4-dimethyl-6-(1'-methylundec-1'-yl)-phenol, 2,4-dimethyl-6-(1'-methylheptadec-1'-yl)-phenol, 2,4-dimethyl-6-(1'-methyltridec-1'-yl)-phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example $\alpha$-, $\beta$-, $\gamma$- and $\delta$-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.6. Alkylidene bisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)-phenol], 2,2'-methylenebis(4-methyl-6-cyclohexylphenol), 2,2'-methylenebis(6-noyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(a-methylbenzyl)-4-nonylphenol], 2,2'-methylenebis[6-($\alpha$,$\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxy-benzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenylidicyclopentadiene, bis[2-(3'-tert-butyl-2'-hydroxy-5'-methylbenzyl)-6-tert-butyl-4-methyohenyl] terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane.

1.7. O-, N- and S-benzyl compounds, for example 3,5,3',5'-tetra-tert-butyl4,4'-dihydroxydibenzyl ether, octadecyl-4-hydroxy-3,5-dimethylbenzyl mercaptoacetate, tridecyl-4-hydroxy-3,5-di-tert-butylbenzyl mercaptoacetate, tris(3,5-di-tert-butyl-4-hydroxybenzyl)amine, bis(4-tert-butyl-3-hydroxy-2,6-dimethylbenzyl) dithioterephthalate, bis(3,5-di-tert-butyl-4-hydroxy-benzyl) sulfide, isooctyl-3,5-di-tert-butyl-4-hydroxybenzyl mercaptoacetate.

1.8. Hydroxybenzylated malonates, for example dioctadecyl 2,2-bis(3,5-di-tert-butyl-2-hydroxybenzyl)malonate, dioctadecyl 2-(3-tert-butyl-4-hydroxy-5-methylbenzyl) malonate, didodecylmercaptoethyl 2,2-bis(3,5-di-tert-butyl-4-hydroxybenzyl)malonate, di-[4-(1,1,3,3-tetramethylbutyl) phenyl] 2,2-bis(3,5-di-tert-butyl-4-hydroxybenzyl) malonate.

1.9. Hydroxybenzyl aromatic compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-trizaine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl) isocyanurate.

1.11. Benzyl phosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, calcium salt of 3,5-di-tert-butyl-4-hydroxybenzylphosphonic acid monoethyl ester.

1.12. Acylaminohenols, for example 4-hydroxylauric acid anilide, 4-hydroxystearic acid anilide, N-(3,5-di-tert-butyl-4-hydroxyphenyl)carbamic acid octyl ester.

1.13. Esters of β-(3,5-di-tert-butyl-4-hydroxyphenyl) propionic acid with mono- or poly-hydric alcohols, for example with methanol, ethanol, n-octanol, iso-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or poly-hydric alcohols, for example with methanol, ethanol, n-octanol, iso-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethyhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or poly-hydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3.5-di-tert-butyl-4-hydroxyphenylacetic acid with mono- or poly-hydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethyihexanediol, trimethylolpropane, 4-hydroxymethyl-1-phospha-2,6,7-trioxabicyclo[2.2.2]octane.

1.17. Amides of β-(3.5-di-tert-butyl-4-hydroxyphenyl) propionic acid, for example N,N'-bis(3,5-di-tert-butyl-4-hydroxyphenylpropionyl) hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl) hydrazide, N,N'-bis[2-[3,5-di-tert-butyl-4-hydroxyphenyl]propionyloxy)ethyl] oxamide (Naugard®XL-1 (Uniroyal)).

1.18. Ascorbic acid (Vitamin C).

1.19. Aminic anti-oxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di-(2-naphthyl)-p-phenylenediamine, N-isopropyl-N'-phenyl-p-phenylenediamine, N-(1,3-dimethyl-butyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)-diphenylamine, N,N'-dimethyl-N,N'-di-sec-butyl-p-phenylenediamine, diphenylamine, N-allyidiphenylamine, 4-isopropoxydiphenylamine, N-phenyl-1-naphthylamine, N-(4-tert-octylphenyl)-1-naphthlamine, N-phenyl-2-naphthylamine, octylated diphenylamine, for example p,p'-di-tert-octyldiphenyiamine, 4-n-butylaminophenol, 4-butyrylaminophenol, 4-nonanoylaminophenol, 4-dodecanoylaminophenol, 4-octadecanoylaminophenol, di-(4-methoxyphenyi)-amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-di-[(2-methyl-phenyl)-amino]ethane, 1,2-di-(phenylamino) propane, (o-tolyl)-biguanide, di-[4-(1', 3'-dimethyl-butyl)-phenyl]amine, tert-octylated N-phenyl-1-naphthylamine, mixture of mono- and di-alkylated tert-butyl-/tert-octyl-diphenylamines, mixture of mono- and di-alkylated nonyldiphenylamines, mixture of mono- and di-alkylated dodecyidiphenylamines, mixture of mono- and di-alkylated isopropyl-/isohexyl-diphenylamines, mixtures of mono- and di-alkylated tert-butyl-diphenylamines, 2,3-dihydro-3,3-dimethyl-4H-1,4-benzothiazine, phenothiazine, mixture of mono- and di-alkylated tert-butyl-/tert-octyl-phenothiazines, mixture of mono- and di-alkylated tert-octylphenothiazines, N-allylphenothiazine, N,N,N',N'-tetraphenyl-1,4-diaminobut-2-ene, N,N-bis(2,2,6,6-tetramethylpiperidin-4-yl)hexamethylenediamine, bis(2,2,6,6-tetramethylpiperidin-4-yl) sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)benzotriazole, 2-(3', 5'-di-tert-butyl-2'-hydroxyphenyl)benzotriazole, 2-(5'-phenyl) benzotriazole, 2-(2'-hydroxy-5'-(1,1,3,3-tetramethylbutyl) phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzctriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)-5-chlorobenzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy,carbonylethyl]-2'-hydroxyphenyl)benzotriazole, 2-(3'-dodecyl-2'-hydroxy-5'-methylphenylbenzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazol-2-yl-phenol]; transesterification product of 2-[3'-tert-butyl-5'-(2-methoxycarbonylethyl)-2'-hydroxyphenyl] benzotriazole with polyethylene glycol 300;

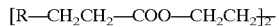

in which R=3'-tert-butyl-4'-hydroxy-5'-2H-benzotriazol-2-yl-phenyl; 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl)phenyl] benzotriazole.

2.2. 2-Hydroxybenzoihenones, for example the 4-hydroxy, 4-methoxy, 4-octyloxy, 4decyloxy, 4-dodecyloxy, 4-benzyloxy, 4,2',4'-trihydroxy, 2'-hydroxy-4,4'-dimethoxy derivative.

2.3. Esters of unsubstituted or substituted benzoic acids, for example 4-tert-butylphenyl salicylate, phenyl salicylate, octyiphenyl salicylate, dibenzoylresorcinol, bis(4-tertbutybenzoyl)resorcinol, benzoylresorcinol, 3,5-di-tert-butyl-4-hydroxybenzoic acid 2,4-di-tert-butylphenyl ester, 3,5-di-tert-butyl-4-hydroxybenzoic acid hexadecyl ester, 3,5-di-tert-butyl-4-hydroxybenzoic acid octadecyl ester, 3,5-di-tert-butyl-4-hydroxybenzoic acid 2-methyl-4,6-di-tert-butylphenyl ester.

2.4. Acrylates, for example α-cyano-β,β-diphenylacrylic acid ethyl ester or isooctyl ester, α-carbomethoxycinnamic acid methyl ester, α-cyano-β-methyl-p-methoxycinnamic acid methyl ester or butyl ester, α-carbomethoxy-p-methoxycinnamic acid methyl ester, N-(β-carbomethoxy-β-cyanovinyl)-2-methylindoline.

2.5. Nickel compounds, for example nickel complexes of 2,2'-thio-bis[4-(1, t,3,3-tetramethylbutyl)phenol], such as the 1:1 or 1:2 complex, optionally with additional ligands, such as n-butylamine, triethanolamine or N-cyclohexyldiethanolamine, nickel dibutyl dithiocarbamate, nickel salts of 4-hydroxy-3,5-di-tert-butylbenzylphosphonic acid monoalkyl esters, such as of the methyl or ethyl ester, nickel complexes of ketoximes, such as of 2-hydroxy-4-methylphenylundecyl ketoxime, nickel complexes of 1-phenyl-4-lauroyl-5-hydroxypyrazole, optionally with additional ligands.

2.6. Sterically hindered amines, for example bis(2,2,6,6-tetramethylpiperidin-4-yl) sebacate, bis(2,2,6,6-tetramethylpiperidin-4-yl) succinate, bis(1,2,2,6,6-pentamethylpiperidin-4-yl) sebacate, bis(1-octyloxy-2,2,6,6-tetramethylpiperidin-4-yl) sebacate, n-butyl-3,5-di-tert-butyl-4-hydroxybenzylmalonic acid bis(1,2,2,6,6-pentamethylpiperidyl) ester, condensation product of 1-hydroxyethyl-2,2,6,6-tetramethyl-4-hydroxypiperidine and succinic acid, linear or cyclic condensation products of N,N'-bis(2,2,6,6-tetramethyl-4-piperidyl) hexamethylenediamine and 4-tert-octylamino-2,6-dichloro-1,3,5-sec-triazine, tris(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro-[4.5]decane-2,4-dione, bis(1-octyloxy-2,2,6,6-tetramethylpiperidyl) sebacate, bis(1-octyloxy-2,2,6,6-tetramethylpiperidyl) succinate, linear or cyclic condensation products of N,N'-bis($_{2,2}$,6,6-tetramethyl-4-piperidyl)hexamethylenediamine and 4-morpholino-2,6-dichloro-1,3,5-triazine, condensation product of 2-chloro-4,6-di-(4-n-butylamino-2,2,6,6-tetramethyl-piperidyl)-1,3,5-triazine and 1,2-bis(3-aminopropylamino)ethane, condensation product of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro-[ 4.5]decane-2,4-dione, 3-dodecyl-1-(2,2,6,6-tetramethyl-4-piperidyl)pyrrolidine-2, 5-dione, 3-dodecyl-1-(1,$_2$,2,6,6-pentamethyl-4-piperidyl)-pyrrolidine-2,5-dione, mixture of 4-hexadecyloxy-4-stearyloxy-2,2,6,6-tetramethylpiperidine, condensation product of N,N'-bis(2,2,6,6-tetramethyl-4-piperidyl) hexamethylenediamine and 4-cyclohexylamino-2,6-dichloro-1,3,5-triazine, condensation product of 1,2-bis(3-aminopropylamino)ethane and 2,4,6-trichloro-1,3,5-triazine and 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4.5]decane, reaction product of 7,7,9,9-tetramethyl-2-cycloundecyl-1-oxa-3,8-diaza-4-oxospiro[4.5]decane and epichlorohydrin, 1,1-bis(1,2,2,6,6-pentamethyl-4-piperidyloxycarbonyl)-2-(4-methoxyphenyl) ether, N ,N'-bis-formyl-N,N'-bis(2,2,6, 6-tetramethyl-4-piperidyl)hexamethylenediamine, diester of 4-methoxymethylenemalonic acid with 1,2,2,6,6-pentamethyl-4-hydroxypiperidine, poly[methylpropyl-3-oxy-4-(2,2,6,6-tetramethy1–4-piperidyl)]siloxane, reaction product of maleic acid anhydride α-olefin copolymer and 2,2,6,6-tetramethyl4-aminopiperidine or 1,2,2,6,6-pentamethyl-4-aminopiperidine.

2.7. Oxalic acid diamides, for example 4,4'-dioctyloxy oxanilide, 2,2'-diethoxy oxanilide, 2,2'-dioctyloxy-5,5'-di-tert-butyl oxanilide, 2,2'-didodecyloxy-5,5'-di-tert-butyl oxanilide, 2ethoxy-2'-ethyl oxanilide, N,N'-bis(3-dimethylaminopropyl) oxalamide, 2-ethoxy-5-tert-butyl-2'-ethyl oxanilide and a mixture thereof with 2-ethoxy-2'-ethyl-5,4'-di-tert-butyl oxanilide, mixtures of o- and p-methoxy- and also of o- and p-ethoxy-di-substituted oxanilides.

2.8. 2-(2-Hydroxyphenyl)-1l,35-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4propyloxyphenyl)-6-(2,4-dimethylphenyl)-3,5-triazine, 2-(2-hydroxy-4-octyloxyphenyl)- 4,6-bis(4-methylphenyl)-1,3,5-triazine, 2-(2-hydroxy-4-dodecyloxyphenyl)-4,6-bis(2,4-dimethyl-phenyl)-1,3,5-triazine, 2-(2-hydroxy-4-tridecyloxyphenyl)-4,6-bis(2,4-dimethylphenyl)-1,3,5-triazine, 2-(2-hydroxy-4-(2-hydroxy-3-butyloxypropyloxy) phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine, 2–14-(dodecyloxy-/tridecyloxy-2-hydroxypropoxy)-2-hydroxyphenyl]-4,6-bis (2,4-dimethylphenyl)-1,3,5-triazine, 2-[2-hydroxy-4-(2-hydroxy-3-dodecyloxypropoxy)-phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropytoxy]phenyl}-4,6-bis(2,4-dimethylphenyl)-1,3,5-triazine.

3. Metal deactivators, for example N,N'-diphenyloxalic acid diamide, N-salicylal-N'-salicyloyl-hydrazine, N,N'-bis(salicyloyl)hydrazine, N,N'-bis(3,5-di-tert-butyl-4-hydroxyphenylpropionyl)hydrazine, 3-salicyloylamino-1,2, 4-triazole, bis(benzylidene)oxalic acid dihydrazide, oxanilide, isophthalic acid dihydrazide, sebacic acid bis-phenylhydrazide, N,N'-diacetyladipic acid dihydrazide, N,N'-bis-salicyloyloxalic acid dihydrazide, N,N'-bis-salicyloythiopropionic acid dihydrazide.

4. Phosphites, phosphines and phosphonites, for example triphenyl phosphite, diphenyl alkyl phosphites, phenyl dialkyl phosphites, tris(nonylphenyl) phosphite, trilauryl phosphite, trioctadecyl phosphite, trimethylphosphine, tri-n-butylphosphine, triphenylphosphine, distearylpentaerythritol diphosphite, tris(2,4-di-tert-butylphenyl)phosphite, diisodecylpentaerythritol diphosphite, bis(2,4-di-tert-butylphenyl)pentaerythritol diphosphite, bis(2,6-di-tert-butyl-4-methylphenyl)pentaerythritol diphosphite, bis-isodecyloxypentaerythritol diphosphite, bis(2,4-di-tert-butyl-6-methylphenyl)pentaerythritol diphosphite, bis(2,4, 6- tri-tert-butylphenyl)-pentaerythritol diphosphite, tristearylsorbitol triphosphite, tetrakis(2,4-di-tert-butylphenyl)-4,4'-biphenylene diphosphonite, 6-isooctyloxy-2,4,8,10-tetra-tert-butyl-12H-dibenz[d,g]-1,
3,2-dioxaphosphocine, 6fluoro-2,4,8,10-tetra-tert-butyl-12-
methyl-dibenz[d,g]-1,3,2-dioxaphosphocine, bis(2,4-di-tert-
butyl-6-methylphenyl) methylphosphite, bis(2,4-di-tert-
butyl-6-methylphenyl) ethylphosphite, 2,2',2"-nitrilo
[triethyl-tris(3,3',5,5'-tetra-tert-butyl-1,1'-biphenyl-2,2'-
diyl)phosphite], 2-ethylhexyl-(3,3',5,5'-tetra-tert-butyl-1,1'-
biphenyl-2,2'-diyl) phosphite.

Use of the following phosphites is especially preferred:

tris(2,4-di-tert-butylphenyl) phosphite (Irgafos® 168,
Ciba Specialty Chemicals),
tris(nonylphenyl) phosphite,

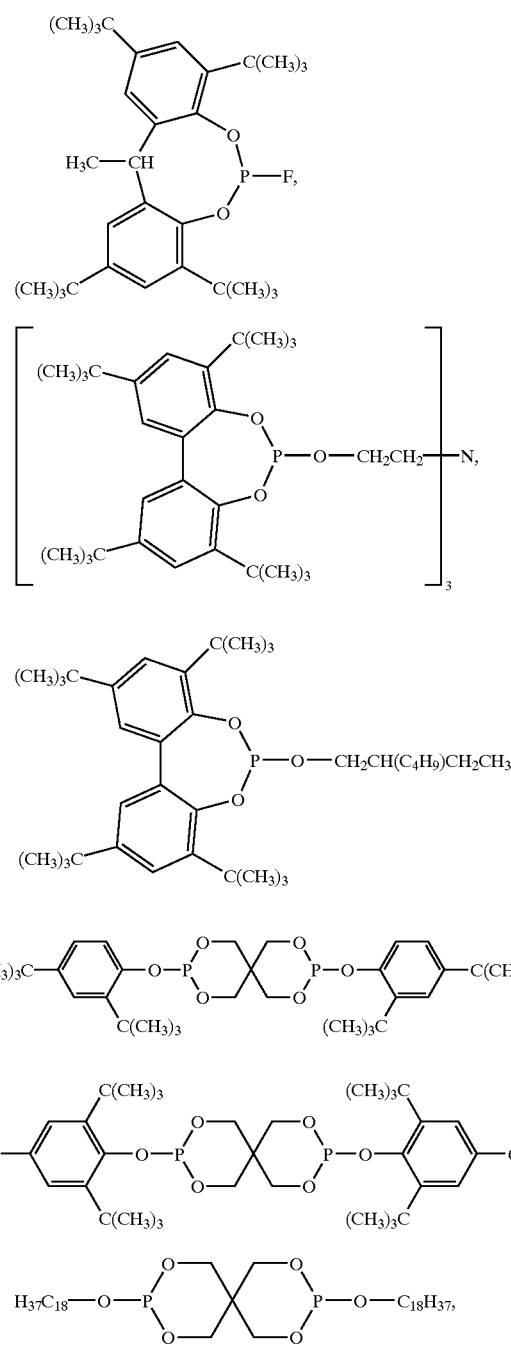

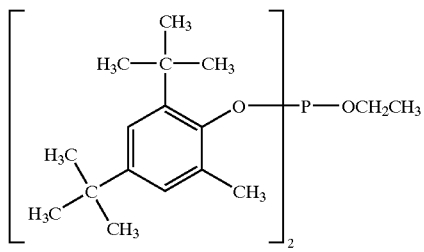

5. Hydroxylamines, for example N,N-dibenzylhydroxylamine, N,N-diethylhydroxylamine, N,N-dioctylhydroxylamine, N,N-dilaurylhydroxylamine, N,N-ditetradecyhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine from hydrogenated tallow fatty amines.

6. Nitrones, for example N-benzyl-alpha-phenyinitrone, N-ethyl-alpha-methyinitrone, N-octyl-alpha-heptylnitrone, N-lauryl-alpha-undecylnitrone, N-tetradecyl-alpha-tridecylnitrone, N-hexadecyl-alpha-pentadecyinitrone, N-octadecyl-alpha-heptadecyinitrone, N-hexadecyl-alpha-heptadecyinitrone, N-octadecyl-alpha-pentadecyinitrone, N-heptadecyl-alpha-hepta-decyinitrone, N-octadecyl-alpha-hexadecyinitrone, nitrones derived from N,N-dialkylhydroxylamines prepared from hydrogenated tallow fatty amines.

7. Thiosynergistic compounds, for example thiodipropionic acid dilauryl ester or thiodipropionic acid distearyl ester.

8. Peroxide-destroying compounds, for example esters of β-thio-dipropionic acid, for example the lauryl, stearyl, myristyl or tridecyl ester, mercaptobenzimidazole, the zinc salt of 2-mercaptobenzimidazole, zinc dibutyidithiocarbamate, dioctadecyidisulfide, pentaerythritol tetrakis(β-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyanodiamide, triallyl cyanurate, urea derivatives, hydrazine derivatives, amines, polyamides, polyurethanes, alkali metal and alkaline earth metal salts of higher fatty acids, for example calcium stearate, zinc stearate, magnesium behenate, magnesium stearate, sodium ricinoleate, potassium palmitate, antimony pyrocatecholate or zinc pyrocatecholate.

11. Nucleating agents, for example inorganic substances, for example talc, metal oxides, such as titanium dioxide or magnesium oxide, phosphates, carbonates or sulfates of preferably alkaline earth metals; organic compounds, such as mono- or poly-carboxylic acids and their salts, for example 4-tert-butylbenzoic acid, adipic acid, diphenytacetic acid, sodium succinate or sodium benzoate; polymeric compounds, for example ionic copolymerisates ("ionomers").

12. Fillers and reinforcing agents, for example calcium carbonate, silicates, glass fibres, glass beads, talc, kaolin, mica, barium sulfate, metal oxides and hydroxides, carbon black, graphite, wood powders, and powders and fibres of other natural products, synthetic fibres.

13. Other additives, for example plasficisers, lubricants, emulsifiers, pigments, rheology additives, catalysts, flow auxiliaries, optical brighteners, flame retardants, antistatics, blowing agents.

14. Benzofuranones and indolinones, as described, for example, in U.S. Pat. No. 4,325,863; U.S. Pat. No. 4,338,244; U.S. Pat. No. 5,175,312, U.S. Pat. No. 5,216,052; U.S. Pat. No. 5,252,643; DE-A-4 316611; DE-A-4 316 622; DE-A-4 316876; EP-A-0 589 839 or EP-A-0 591 102, or 3-[4-(2-acetoxyethoxy)phenyl]-5,7-di-tert-butyl-benzofuran-2-one, 5,7-di-tert-butyl-3-[4-(2-stearoyloxy-ethoxy)phenyl]-benzofuran-2-one, 3,3'-bis[5,7-di-tert-butyl-3-(4-[2-hydroxyethoxy]phenylbenzofuran-2-one), 5,7-di-tert-butyl-3-(4-ethoxyphenyl)-benzofuran-2-one, 3-(4-acetoxy-3,5-dimethylphenyl)-5,7-di-tert-butyl-benzofuran-2-one, 3-(3,5-dimethyl4-pivaloyloxy-phenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The invention relates also to a process for the preparation of metathesis polymerisates, which process comprises heating a composition comprising (α) dicyclopentadiene or a further strained cycloolefin or dicyclopentadiene in admixture with a further strained cycloolefin and (β) a catalytic amount of at least one compound of formula Ia or Ib, wherein $L^1$, X, Y, A, Z, R and Het-N have the definitions mentioned, or an isomer thereof, and, optionally, further additives for polymers, and optionally subjecting the obtainable metathesis polymerisate to a shaping process. The process according to the invention is preferably carried out at a temperature of at least 0° C. The process according to the invention is especially carried out at temperatures of from 0° to 300° C., preferably from room temperature to 250° C., especially from room temperature to 200° C. and more especially from room temperature to 160° C. After the polymerisation it may be advantageous to after-bake the polymers at elevated temperatures, for example from 80 to 200° C. For the preparation of linear polymers, the reaction is preferably carried out in dilute solutions.

The polymerisaion may be combined with shaping processes, for example calendering, casting, pressing, injection-moulding or extrusion processes. Using the process according to the invention it is possible to produce materials for the manufacture of shaped articles by machining techniques or thermoplastically deformable materials for the manufacture of shaped articles of every kind and coatings. Shaping and polymerisation are advantageously combined in solvent-free reactive systems, it being possible to use processing methods, such as, for example, injection-moulding, extrusion, and polymerisation in pre-defined moulds (optionally under pressure).

The invention relates also to the polymerisates obtainable by the process according to the invention.

Among the polymers, preference is given to those that comprise only carbon and hydrogen.

The polymerisates prepared according to the process of the invention may be homopolymers or copolymers having a random distribution of structural units, or may be graft polymers or block polymers, as well as cross-linked polymers of that kind. They may have an average molecular weight ($\overline{Mw}$) of, for example, from 500 to 2 million Daltons, preferably from 1000 to 1 million Daltons (determined according to GPC by comparison with polystyrene standards having a narrow distribution).

It has been found, surprisingly, that the polymerisation leads in high yields to a polydicyclopentadiene that corresponds to a linear polymer or copolymer having structural units of the formula

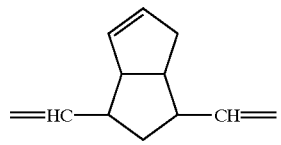

and represents a preferred subject of the invention. A further preferred subject of the invention is formed by cross-linked copolymers having structural units of the formula

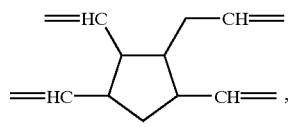

which can be prepared according to the process of the invention.

The non-cross-linked or linear polymers include oligomers and polymers and may contain, for example, from 5 to 5000, advantageously from 10 to 2000, preferably from 20 to 1000, especially from 20 to 500, and more especially from 20 to 300, structural units. If the polymers are processed further, relatively low molecular weights are preferred and if processing into shaped articles is carried out, polymers having relatively high molecular weights are expediently used.

Depending on the nature and amount of the monomers used, the polymers according to the invention can have different properties. Some are distinguished by a very high oxygen permeability, outstanding dielectric properties (low dielectric constants, low loss factors or tan δ values), good thermal stability (glass transition temperatures above 100° C.), good toughness properties (impact strength and notched bar impact strength), flexibility and mechanical strength properties (fracture strength), hardness and low water absorption. Others have outstanding optical properties, for example high transparency and low refractive indices. Special attention should also be drawn to the low degree of shrinkage and the excellent surface properties (smoothness, gloss, adhesive strength). They may therefore be used in a wide variety of technical fields.

As coatings on the surfaces of carrier materials the polymers according to the invention are distinguished by a high adhesive strength. Furthermore, the coated materials are distinguished by a high surface smoothness and gloss. Among the good mechanical properties, special attention should be drawn to the low degree of shrinkage and the high impact strength, as well as the thermal stability. Furthermore, the ease of demoulding and the high solvent resistance should be mentioned. The surfaces may be further modified, for example surface-coated or printed; in this case too, mention should be made of the high adhesive strength of the surface coatings.

The polymers obtainable according to the invention are especially suitable for the manufacture of consumer articles of every kind, for example shaped articles for cars, boats, leisure articles, pallets, tubes, panels etc.; as insulation material for the manufacture of electrical and electronic components; as implants; as binders for surface coatings; as thermosetting compositions for model-making or as bonding agents for bonding substrates having low surface energies (TEFLON, polyethylene or polypropylene). The compositions according to the invention may be used also in the preparation of surface coatings by thermopolymerisation, it being possible to use, on the one hand, clear (transparent) and even pigmented compositions. Both white and coloured pigments may be used. Furthermore, mention should be made of the manufacture of shaped articles by thermoplastic shaping processes for consumer articles of every kind.

The compositions according to the invention are also especially suitable for the manufacture of protective coatings. The invention relates also to a variant of the process according to the invention for the manufacture of coated materials, which comprises applying the composition according to the invention and, optionally, solvents in the form of a coating to a carrier, for example by immersion, spreading, pouring, roller application, knife application or centrifugal casting processes, optionally removing the solvent and heating the coating for the purpose of polymerisation. By means of that process it is possible for surfaces of substrates to be modified or protected (corrosion protection).

The present invention further relates to a coated carrier material wherein a coating of the polymerisate according to the invention has been applied to a substrate.

The present invention relates also to a coated substrate having a cured coating of the polymerisate according to the invention.

Suitable substrates (carrier materials) are, for example, those made from glass, minerals, ceramics, plastics, wood, semi-metals, metals, metal oxides and metal nitrides. The coating thickness depends essentially on the desired use and may be, for example, from 0.1 to 1000 μm, preferably from 0.5 to 500 μm, especially from 1 to 100 μm. The coated materials are distinguished by a high adhesive strength and good thermal and mechanical properties.

The coated materials according to the invention may be manufactured by known methods, for example, spreading, knife application, pouring processes, such as curtain pouring, or centrifugal casting.

In the case of coatings, especially good results are frequently obtained when there are additionally used, for the thermal metathesis polymerisation, cycloolefins that additionally contain from 1 to 3, preferably 1, further double bond(s) and that represent, within the context of the invention, polycyclic fused ring systems.

The following Examples illustrate the invention in more detail:

EXAMPLE 1 a) Preparation of:

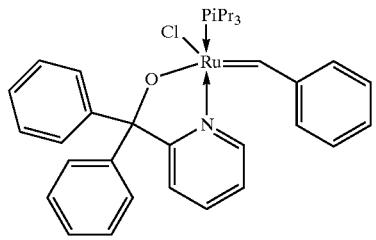

2.5 ml of a 1.6 molar solution of n-butyllithium in hexane are added dropwise at −700° C. to a solution of 1.05 g of (α,α-diphenyl-2-pyridylmethanol in 60 ml of diethyl ether. Stirring is then carried out for 15 minutes. The white suspension obtainable is added dropwise to a solution of 2.34 g of $RuCl_2(=CHC_6H_5)(PiPr_3)_2$ in 60 ml of toluene. The reaction mixture is then allowed to warm slowly to room temperature and stirring is carried out for a further two hours. The reaction mixture is concentrated in vacuo and the residue is extracted with 60 ml of methylene chloride. After evaporating off the solvent, the residue is washed twice with 10 ml of hexane. The product is obtained in the form of a green powder in a yield of 69%. Carbene-H signal in $^1$H NMR (CDCl$_3$): δ=17.6 (d, J=17.7 Hz); $^{31}$P NMR (CDCl$_3$): δ=49.5; elemental analysis calculated for $C_{34}H_{41}ClNOPRu$: C: 63.1; H: 6.4; N: 2.2 [%]. Found: C: 62.4; H: 6.2; N: 2.1 [%].

b) Preparation of:

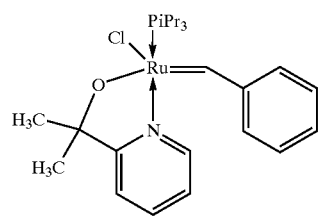

Analogously to Example 1 a), by reacting α,α-dimethyl-2-pyridylmethanol with $RuCl_2(=CHC_6H_5)(PiPr_3)_2$, the catalyst according to the formula drawing is obtained in a 72% yield. Carbene-H signal in $^1$H NMR (CDCl$_3$): δ=17.5 (d, J=17.5 Hz); 31P NMR (CDCl$_3$): δ=51.1; elemental analysis calculated for $C_{24}H_{37}ClNOPRu$: C: 55.1; H: 7.1; N: 2.7 [%]. Found: C: 55.4; H: 7.2; N: 2.9 [%].

c) Preparation of:

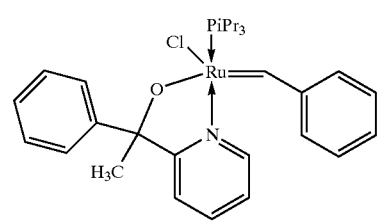

Analogously to Example 1 a), by reacting α-methyl-α-phenyl-2-pyridylmethanol with $RuCl_2(=CHC_6H_5)(PiPr_3)_2$, the catalyst according to the formula drawing is obtained in a 65% yield. Carbene-H signal in $^1$H NMR (CDCl$_3$): δ=17.8 (d, J=17.4 Hz); $^{31}$P NMR (CDCl$_3$): δ=51.2; elemental analysis calculated for $C_{29}H_{39}ClNOPRu$: C: 59.5; H: 6.7; N: 2.4 [%]. Found: C: 60.4; H: 7.1; N: 2.4 [%].

d) Preparation of:

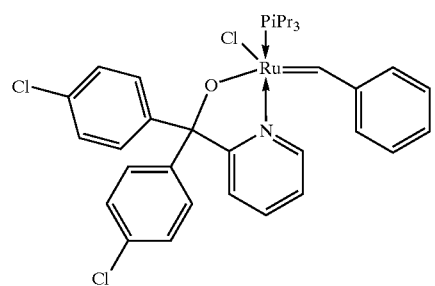

Analogously to Example 1 a), by reacting α,α-bis(4-chlorophenyl)-2-pyridylmethanol with $RuCl_2(=CHC_6H_5)(PiPr_3)_2$, the catalyst according to the formula drawing is obtained in a 72% yield. Carbene-H signal in $^1$H NMR (CDCl$_3$): δ=17.6 (d, J=17.8 Hz); $^{31}$P NMR (CDCl$_3$): δ=49.7; elemental analysis calculated for $C_{34}H_{39}Cl_3NOPRu$: C: 57.0; H: 5.5; N: 2.0 [%]. Found: C: 58.0; H: 5.9; N: 2.1 [%].

e) Preparation of:

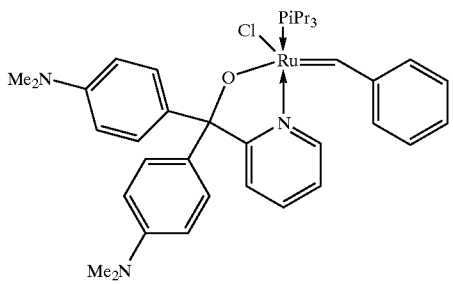

Analogously to Example 1, by reacting α,α-bis(4-dimethylaminophenyl)-2-pyridylmethanol with RuCl$_2$(=CHC$_6$H$_5$)(PiPr$_3$)$_2$, the catalyst according to the formula drawing is obtained in a 78% yield. Carbene-H signal in $^1$H NMR (CDCl$_3$): δ=17.7 (d, J=17.6 Hz); $^{31}$P NMR (CDCl$_3$): δ=49.4; elemental analysis calculated for C$_{38}$H$_{51}$ClN$_3$OPRu: C: 62.2; H: 7.0; N: 5.7 [%]. Found: C: 62.9; H: 6.9; N: 6.0 [%].

f) Preparation of:

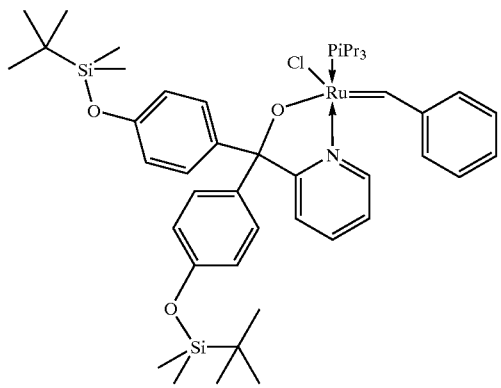

Analogously to Example 1a), by reacting α,α-bis[4-(tert-butyldimethylsilyloxy)phenyl]-2-pyridylmethanol, the catalyst according to the formula drawing is obtained in a 72% yield. Carbene-H signal in $^1$H NMR (CDCl$_3$): δ=17.7 (d, J=17.8 Hz); $^{31}$P NMR (CDCl$_3$): δ=49.9.

g) Preparation of:

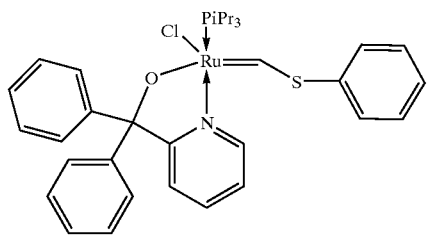

Analogously to Example 1a), by reacting α,α-diphenyl-2-pyridylmethanol with RuCl$_2$(=CHSC$_6$H$_5$)(PiPr$_3$)$_2$, the catalyst according to the formula drawing is obtained in a 56% yield. Carbene-H signal in $^1$H NMR (CDCl$_3$): δ=15.3 (d, J=15.3 Hz); 31P NMR (CDCl$_3$): δ=51.8.

h) Preparation of:

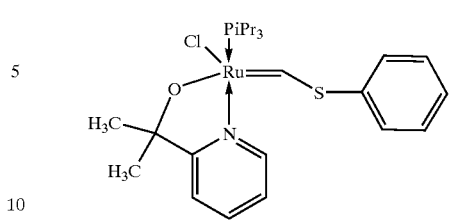

Analogously to Example 1a), by reacting α,α-dimethyl-2-pyridylmethanol with RuCl$_2$(=CHSC$_6$H$_5$)(PiPr$_3$)$_2$, the catalyst according to the formula drawing is obtained in a 86% yield. Carbene-H signal in $^1$H NMR (CDCl$_3$): δ=15.4 (d, J=14.8 Hz); $^{31}$P NMR (CDCl$_3$): δ=52.4; elemental analysis calculated for C$_{24}$H$_{37}$ClNOPRuS: C: 51.9; H: 6.7; N: 2.5. Found: C: 51.1; H: 6.9; N: 2.7 [%].

EXAMPLE 2

Cyclisation of Diethyldiallyl Malonate:

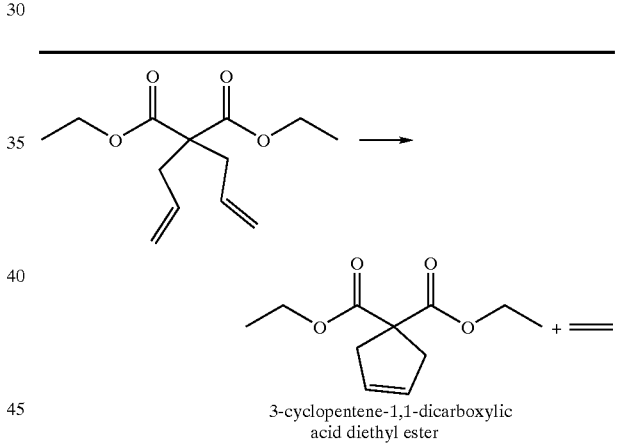

3-cyclopentene-1,1-dicarboxylic acid diethyl ester

| catalyst Ex. 1 | solvent | concentration cat. in diene | concentration diene | duration | temperature | yield |
|---|---|---|---|---|---|---|
| a) | 1,1,1-trichloroethane | 0.5 mol % | 0.31 molar | 4 h | 60° C. | 100% |
| b) | 1,1,1-trichloroethane | 1 mol % | 0.15 molar | 30 min | 60° C. | 100% |

EXAMPLE 3

Cyclisation of N,N'-di-2-propenylcarbamic acid 1,1-dimethylethyl ester:

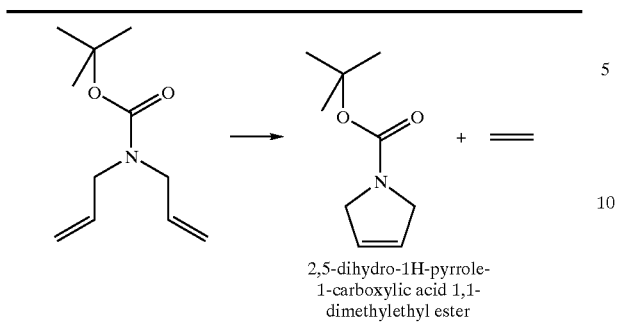

| catalyst Ex. 1 | solvent | concentration cat. in diene | concentration diene | duration | temperature | yield |
|---|---|---|---|---|---|---|
| a) | chloroform | 1 mol % | 0.1 molar | 30 min | 60° C. | 100% |
| b) | chloroform | 1 mol % | 0.1 molar | 30 min | 60° C. | 100% |

EXAMPLE 4

Cyclisation of the 5-Hexenyl Ester of 10-Undecenoic Acid:

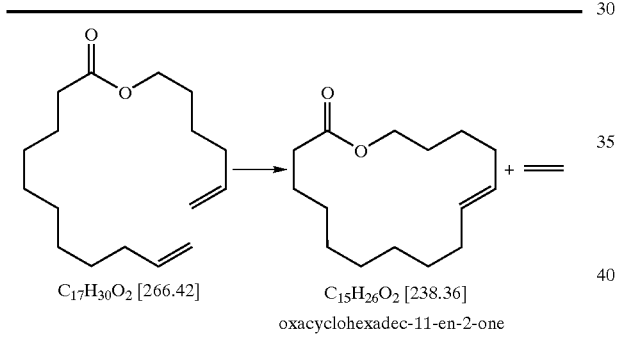

| catalyst | solvent | concentration cat. in diene | concentration diene | duration | temperature | yield |
|---|---|---|---|---|---|---|
| Ex. 1 a) | toluene | 10 mol % | 0.005 molar | 7 h | 60° C. | 50% |

EXAMPLE 5

Polymerisation of DCPD:

3.5 mg of catalyst (Example 1a)) are dissolved in 10.0 g of dicyclopentadiene (BF Goodrich, purity: 98%). A DSC (=Differential Scanning Calorimetry) recording is taken of approximately 10 mg of the resulting mixture (temperature range: 0° to 250° C., heating rate: 10° C./min). The following result is obtained:

Onset temperature of exotherm: 106° C.; maximum of exotherm at T=130° C.: ΔH=304 J/g.

In a second run, also using DSC, a glass transition temperature ($T_g$) of 155° C. is measured. The mixture remains stable (that is to say, there is no discernible increase in viscosity) at room temperature for more than 24 hours but, on heating at 100° C., fully cures within two hours. After post-curing for one hour at 150° C., a $T_g$ of 150° C. is measured.

What is claimed is:

1. A compound of formula

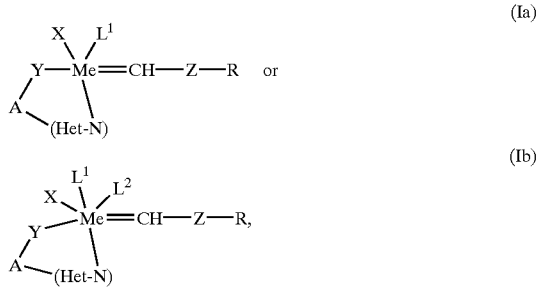

wherein Me is ruthenium or osmium;
$L^1$ and $L^2$ are neutral ligands having electron donor properties;
X is an anionic ligand;
Y is oxygen or sulfur;
A is a direct bond, $C_1$–$C_4$alkylene or $C_2$–$C_4$alkylidene;
Z is a direct bond, oxygen, sulfur or the groups

wherein $R_1$ and $R_2$ are hydrogen or hydrocarbon radicals;
R is a hydrocarbon radical; and
Het-N is mono- or bi-cyclic, aromatic heterocyclyl having at least one nitrogen atom that is coordinated with Me; and isomers thereof.

2. A compound according to claim 1, wherein formula Ia includes the isomeric structures of formulae

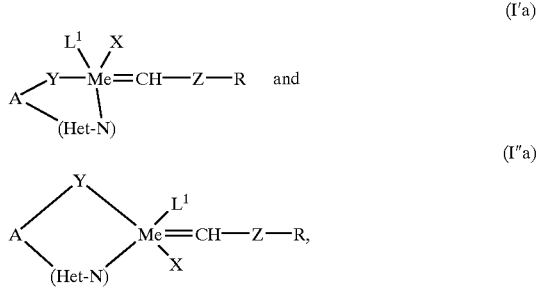

wherein $L^1$, X, Y, A, Z, R and Het-N are as defined in claim 1.

3. A compound of formula Ia or Ib according to claim 1, wherein Me is ruthenium.

4. A compound of formula Ia or Ib according to claim 1, wherein the anionic ligand X is derived from halides, fluoro complexes, anions of oxy acids, sulfonates, phosphonates, carboxylates, alcoholates, acetylides or from cyclopentadiene and the neutral ligands $L^1$ and $L^2$ are tertiary phosphine.

5. A compound of formula Ia or Ib according to claim 4, wherein the tertiary phosphine corresponds to a compound selected from the group (iso-$C_3H_7$)$_3$P, (sec-$C_4H_9$)$_3$P, ($C_5H_9$)$_3$P and ($C_6H_{11}$)$_3$P.

6. A compound of formula Ia or Ib according to claim 1, wherein Het-N denoting monocyclic heterocyclyl contains, in total, from one to three nitrogen heteroatoms and five or six ring atoms and Het-N denoting bicyclic heterocyclyl contains, in total, from one to four nitrogen heteroatoms and from seven to twelve ring atoms.

7. A compound of formula Ia or Ib according to claim 6, wherein monocyclic heterocyclyl containing, in total, from one to three nitrogen heteroatoms and five or six ring atoms is selected from the group consisting of pyrrole, imidazole, pyrazole, pyridine, pyrimidine, pyrazine, pyridazine and triazine, and bicyclic heterocyclyl containing, in total, from one to four nitrogen heteroatoms and from seven to twelve ring atoms is selected from the group indole, quinoline, isoquinoline, purine and pteridine.

8. A compound of formula Ia or Ib according to claim 6, wherein Y is oxygen and, when Het-N is bicyclic heterocyclyl, A is a direct bond or, when Het-N is monocyclic heterocyclyl, is $C_1$–$C_4$alkylene or $C_2$–$C_4$alkylidene, and Z is a direct bond or is sulfur.

9. A compound of formula Ia or Ib according to claim 1, wherein the radicals $R_1$ and $R_2$ in groups B and C are hydrogen, $C_1$–$C_{20}$alkyl, $C_3$–$C_8$cycloalkyl, $C_3$–$C_7$heterocycloalkyl, $C_6$–$C_4$aryl or $C_4$–$C_{15}$heteroaryl, wherein alkyl, cycloalkyl, heterocycloalkyl, aryl and heteroaryl are unsubstituted or substituted by one or more substituents from the group $C_1$–$C_4$alkyl, $C_1$–$C_4$haloalkyl, $C_1$–$C_4$alkoxy, $C_6$–$C_{10}$aryl, $C_6$–$C_{10}$aryloxy, —$NO_2$ and halogen.

10. A compound of formula Ia or Ib according to claim 1, wherein R is phenyl that is unsubstituted or substituted by one or more substituents from the group consisting of $C_1$–$C_6$alkyl, $C_1$–$C_6$alkoxy, $C_1$–$C_6$haloalkyl, hydroxy, nitro, carboxy, sulfo, ammonium and halogen.

11. A compound of formula Ia according to claim 1, wherein $L^1$ is (iso-$C_3H_7$)$_3$P, (sec-$C_4H_9$)$_3$P, ($C_5H_9$)$_3$P or ($C_6H_{11}$)$_3$P; X is chlorine; Y is oxygen; A is methylene, methylene substituted by ethylenedioxy, one or two hydroxy, one or two phenyl or by one or two substituted phenyl from the group 4-chlorophenyl, 4-dimethylaminophenyl and 4-tert-butyldimethylsilylphenyl, ethylidene, or ethylidene or isopropylidene 1- or 2-substituted by phenyl; Z is a direct bond or is sulfur; R is $C_1$–$C_4$alkyl, phenyl or phenyl substituted by $C_1$–$C_4$alkyl; and N-Het is pyridyl that is coordinated in the 1-position with Me and connected in the 2-position to A, and isomers thereof.

12. A compound according to claim 1 of formula (I'a)

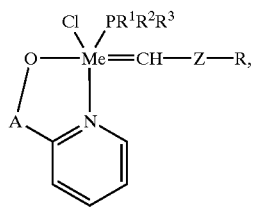

wherein $R^1$, $R^2$ and $R^3$ are isopropyl, sec-butyl, cyclopentyl or cyclohexyl; A is methylene, methylene substituted by ethylenedioxy, one or two hydroxy, one or two phenyl or by one or two substituted phenyl from the group 4-chlorophenyl, 4-dimethylaminophenyl and 4-tert-butyldimethylsilylphenyl, ethylidene, or ethylidene or isopropylidene 1- or 2-substituted by phenyl; Z is a direct bond or is sulfur and R is $C_1$–$C_4$alkyl, phenyl or phenyl substituted by $C_1$–$C_4$alkyl, and isomers thereof.

13. A compound according to claim 12 of formula I'a, wherein $R^1$, $R^2$ and $R^3$ are isopropyl or cyclohexyl; A is methylene, methylene substituted by ethylenedioxy, one or two hydroxy, one or two phenyl or by one or two substituted phenyl from the group 4-chlorophenyl, 4-dimethylaminophenyl and 4-tert-butyldimethylsilylphenyl, ethylidene, or ethylidene or isopropylidene 1- or 2-substituted by phenyl; Z is a direct bond and R is phenyl, and isomers thereof.

14. A process for the preparation of a compound of formula Ia or Ib, which process comprises reacting a compound of formula (IIIa)

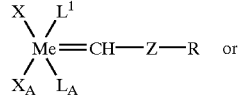

or (IIIb)

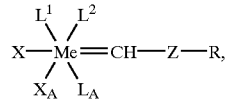

wherein $X_A$ and $L_A$ are leaving groups of the substrate and $L^1$, $L^2$, X, Z and R are as defined for formulae Ia and Ib, with a hydroxy or mercapto compound of formula H-Y-A-(Het-N)      (IV), wherein Y, A and Het are as defined for formulae Ia and Ib, or with a reactive functional derivative thereof, with $X_A$ and $L_A$ being removed, and, if desired, isolating an obtained compound of formula Ia or Ib and/or reacting an obtained compound of formula Ia or Ib to form a different compound of formula Ia or Ib.

* * * * *